(12) United States Patent
Heard et al.

(10) Patent No.: US 8,808,287 B2
(45) Date of Patent: Aug. 19, 2014

(54) SUCTION COAGULATOR

(71) Applicant: Covidien LP, Mansfield, MA (US)

(72) Inventors: David N. Heard, Boulder, CO (US); Joe D. Sartor, Longmont, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/710,001

(22) Filed: Dec. 10, 2012

(65) Prior Publication Data

US 2013/0103033 A1    Apr. 25, 2013

Related U.S. Application Data

(62) Division of application No. 12/179,206, filed on Jul. 24, 2008, now Pat. No. 8,328,804.

(51) Int. Cl.
*A61B 18/14* (2006.01)

(52) U.S. Cl.
USPC .............................................. 606/49; 604/35

(58) Field of Classification Search
CPC ............................................ A61B 2108/00023
USPC ................................. 606/49; 600/35; 604/35
See application file for complete search history.

(56) References Cited

U.S. PATENT DOCUMENTS

| | | | |
|---|---|---|---|
| 2,808,833 A | 10/1957 | August | |
| 3,630,203 A | 12/1971 | Sellinger et al. | |
| 3,828,780 A | 8/1974 | Morrison, Jr. | |
| 3,838,242 A | 9/1974 | Goucher | |
| 3,971,383 A | 7/1976 | van Gerven | |
| 3,974,833 A * | 8/1976 | Durden, III ..................... | 604/20 |
| 4,869,715 A | 9/1989 | Sherburne | |
| 4,932,952 A | 6/1990 | Wojciechowicz, Jr. | |
| 4,949,734 A | 8/1990 | Bernstein | |
| 5,084,045 A | 1/1992 | Helenowski | |
| 5,277,696 A * | 1/1994 | Hagen ............................. | 606/49 |

(Continued)

FOREIGN PATENT DOCUMENTS

| | | |
|---|---|---|
| DE | 2429021 A1 | 1/1976 |
| DE | 2460481 A1 | 6/1976 |

(Continued)

OTHER PUBLICATIONS

European Search Report for EP 09 00 9623 dated Sep. 29, 2009.

(Continued)

*Primary Examiner* — Lee S Cohen

(57) ABSTRACT

An electrosurgical suction coagulator is disclosed having improved thermal insulation between the active electrode and adjacent tissue. In embodiments, passive insulation is used to control the transfer of thermal energy from an electrosurgical electrode into surrounding tissue. Braided, closed-sell foam material, and open cell foam materials may be used to thermally insulate the outer surface of a suction coagulator shaft from an inner electrode. In embodiments, a suction coagulator shaft includes an external covering formed from open-cell foam material, which may be saturated with a coolant, such as water or saline, to increase the thermal mass of the shaft. In other embodiments, active cooling delivers coolant to the operative site. In yet other embodiments, a suction coagulator shaft includes a cooling jacket through which coolant is passed to actively cool the instrument. The improved electrosurgical suction coagulator disclosed herein may have a reduced operating surface temperatures which may result in reduced risk of undesirable effects to adjacent tissue, and may result in reduced operative times and improved patient outcomes.

3 Claims, 10 Drawing Sheets

(56) References Cited

U.S. PATENT DOCUMENTS

| | | | |
|---|---|---|---|
| 5,312,401 A | 5/1994 | Newton et al. | |
| 5,364,395 A | 11/1994 | West, Jr. | |
| 5,462,521 A | 10/1995 | Brucker et al. | |
| 5,472,441 A | 12/1995 | Edwards et al. | |
| 5,520,685 A | 5/1996 | Wojciechowicz | |
| 5,647,871 A | 7/1997 | Levine et al. | |
| 5,718,702 A | 2/1998 | Edwards | |
| 5,730,742 A | 3/1998 | Wojciechowicz | |
| 5,807,395 A | 9/1998 | Mulier et al. | |
| 5,814,044 A | 9/1998 | Hooven | |
| 5,848,986 A | 12/1998 | Lundquist et al. | |
| 5,944,713 A | 8/1999 | Schuman | |
| 5,951,546 A | 9/1999 | Lorentzen | |
| 5,951,548 A | 9/1999 | DeSisto et al. | |
| 5,957,882 A | 9/1999 | Nita et al. | |
| 5,968,042 A | 10/1999 | Ernster | |
| 6,027,501 A | 2/2000 | Goble et al. | |
| 6,033,375 A | 3/2000 | Brumbach | |
| 6,039,730 A * | 3/2000 | Rabin et al. | 606/23 |
| 6,053,912 A | 4/2000 | Panescu et al. | |
| 6,063,081 A | 5/2000 | Mulier et al. | |
| 6,117,134 A | 9/2000 | Cunningham et al. | |
| 6,179,803 B1 | 1/2001 | Edwards et al. | |
| 6,190,381 B1 | 2/2001 | Olsen et al. | |
| 6,379,348 B1 | 4/2002 | Onik | |
| 6,379,350 B1 | 4/2002 | Sharkey et al. | |
| 6,406,476 B1 | 6/2002 | Kirwan, Jr. et al. | |
| 6,458,126 B1 | 10/2002 | Doyle | |
| 6,514,251 B1 * | 2/2003 | Ni et al. | 606/41 |
| 6,595,990 B1 | 7/2003 | Weinstein et al. | |
| 6,723,094 B1 * | 4/2004 | Desinger | 606/50 |
| 6,770,070 B1 | 8/2004 | Balbierz | |
| 6,849,073 B2 | 2/2005 | Hoey et al. | |
| 6,911,029 B2 | 6/2005 | Platt | |
| 7,169,148 B2 | 1/2007 | O'Halloran | |
| 7,537,594 B2 | 5/2009 | Sartor | |
| 7,572,257 B2 | 8/2009 | Whayne et al. | |
| 7,588,057 B2 * | 9/2009 | Bentley | 138/127 |
| 8,157,799 B2 * | 4/2012 | Desinger et al. | 606/50 |
| 8,328,804 B2 | 12/2012 | Heard et al. | |
| 2002/0049438 A1 | 4/2002 | Sharkey et al. | |
| 2003/0065316 A1 | 4/2003 | Levine et al. | |
| 2003/0181904 A1 | 9/2003 | Levine et al. | |
| 2004/0082951 A1 | 4/2004 | O'Halloran | |
| 2004/0193150 A1 | 9/2004 | Sharkey et al. | |
| 2004/0260280 A1 | 12/2004 | Sartor | |
| 2005/0187544 A1 | 8/2005 | Swanson et al. | |
| 2007/0118144 A1 | 5/2007 | Truckai et al. | |
| 2007/0233148 A1 | 10/2007 | Truckai et al. | |
| 2008/0161890 A1 * | 7/2008 | Lafontaine | 607/105 |

FOREIGN PATENT DOCUMENTS

| | | |
|---|---|---|
| DE | 3045996 A1 | 7/1982 |
| DE | 3710489 A1 | 11/1987 |
| DE | 4139029 A1 | 6/1993 |
| DE | 4326037 A1 | 2/1995 |
| DE | 9117019.2 | 4/1995 |
| DE | 19537897 A1 | 3/1997 |
| DE | 9117299 U1 | 3/2000 |
| DE | 19848784 A1 | 5/2000 |
| DE | 29724247 U1 | 8/2000 |
| EP | 0186369 A1 | 7/1986 |
| EP | 0447121 A2 | 9/1991 |
| EP | 0612535 A1 | 8/1994 |
| EP | 0956827 A1 | 11/1999 |
| EP | 1050277 A1 | 11/2000 |
| EP | 1050279 A1 | 11/2000 |
| EP | 1082945 A1 | 3/2001 |
| EP | 1090597 A1 | 4/2001 |
| EP | 1090598 A1 | 4/2001 |
| EP | 1090599 A1 | 4/2001 |
| EP | 1127551 A1 | 8/2001 |
| EP | 1199037 A2 | 4/2002 |
| EP | 1199038 A2 | 4/2002 |
| EP | 1293171 A2 | 3/2003 |
| EP | 1323384 A2 | 7/2003 |
| EP | 1561430 A1 | 8/2005 |
| EP | 1570798 A2 | 9/2005 |
| EP | 1595507 A2 | 11/2005 |
| EP | 1602337 A1 | 12/2005 |
| EP | 1 645 234 A1 | 4/2006 |
| EP | 1656900 A2 | 5/2006 |
| FR | 1340509 A | 10/1963 |
| FR | 2 235 669 A1 | 1/1975 |
| GB | 1014995 A | 12/1965 |
| GB | L014995 | 12/1965 |
| GB | 1222243 A | 2/1971 |
| JP | 61-159953 A | 7/1986 |
| SU | 1438745 A1 | 11/1988 |
| WO | 9113593 A1 | 9/1991 |
| WO | 9303678 A1 | 3/1993 |
| WO | 94/20032 A1 | 9/1994 |
| WO | 9627337 A1 | 9/1996 |
| WO | 96/39086 A1 | 12/1996 |
| WO | 9711647 A1 | 4/1997 |
| WO | 98/43264 | 10/1998 |
| WO | 9915091 A1 | 4/1999 |
| WO | 0162333 A1 | 8/2001 |
| WO | 01/64122 A1 | 9/2001 |
| WO | 0247568 A1 | 6/2002 |
| WO | 02058762 A2 | 8/2002 |
| WO | 2004/010883 A1 | 2/2004 |
| WO | 2004/045436 A1 | 6/2004 |
| WO | 2004/073753 A2 | 9/2004 |
| WO | 2005016142 A1 | 2/2005 |
| WO | 2005/060849 A1 | 7/2005 |

OTHER PUBLICATIONS

Grund et al., "Endoscopic Argon Plasma . . . Flexible Endoscopy" Surgery and Allied Technologies, No. 1, vol. 2, pp. 42-46 (Feb. 1994).
Farin et al. "Technology of Argon Plasma . . . Endoscopic Applications" Endoscopic Surgery and Allied Technologies, No. 1, vol. 2, pp. 71-77 (Feb. 1994).
Brand et al. "Electrosurgical Debulking of Ovarian Cancer: A New Technique Using the Argon Beam Coagulator" Gynecologic Oncology 39.
Hernandez et al. "A Controlled Study of the Argon Beam Coagulator for Partial Nephrectomy" The Journal of Urology, vol. 143, May (J.Urol. 143: 1062-1065, 1990).
Ward et al. "A Significant New Contribution to Radical Head and Neck Surgery" Arch Otolaryngol Head Neck Surg., vol. 115, Aug. 1989 pp. 921-923.
Mark H. Mellow, "The Role of Endoscopic Laser Therapy in Gastrointestinal Neoplasms" Advanced Therapeutic Endoscopy, pp. 17-21.
Silverstein et al., "Thermal Coagulation Therapy for Upper Gastrointestinal Bleeding" Advanced Therapeutic Endoscopy, pp. 79-84.
Waye et al., "Techniques in Therapeutic Endoscopy", W.B.Saunders Company, Philadelphia, PA., pp. 1.7-1.15.
European Search Report for 01102843.8-2305 dated May 15, 2001.
International Search Report PCT/US98/19284, dated Jan. 14, 1999.
European Search Report for EP 05002257. 3 dated Jun. 1, 2005.
International Search Report for EP 06019572 dated Nov. 21, 2006.
European Search Report EP 07 00 4356 dated Jul. 2, 2007.
European Search Report EP 07 00 4659 dated Mar. 5, 2008.
European Search Report EP 00 12 1241 dated Jan. 17, 2001.
Valleylab in the OR; Tonsillectomy Article; Aug. 2005.
Valleylab Suction Coagulators; May 2009.
International Search Report from PCT-US03-37111 dated Jul. 21, 2004.
International Search Report from PCT-US04-04685 dated Aug. 6, 2004.
International Search Report from EP-0401-5980 dated Sep. 30, 2004.
International Search Report from PCT-US03-22900 dated Nov. 20, 2003.
International Search Report from EP 05019882.9 dated Feb. 16, 2006.

(56) References Cited

OTHER PUBLICATIONS

International Search Report from EP 05021777.7 dated Feb. 23, 2006.
International Search Report from EP 06014461.5 dated Oct. 31, 2006.
International Search Report from EP 07009028 dated Jul. 16, 2007.
International Search Report from EP 06 00 5540 dated Sep. 24, 2007.
International Search Report from EP 08 00 2357 dated Jun. 30, 2008.
Examination Report EP09009623.1 dated Nov. 9, 2010.
European Search Report No. EP09009623 dated Sep. 29, 2009.

* cited by examiner

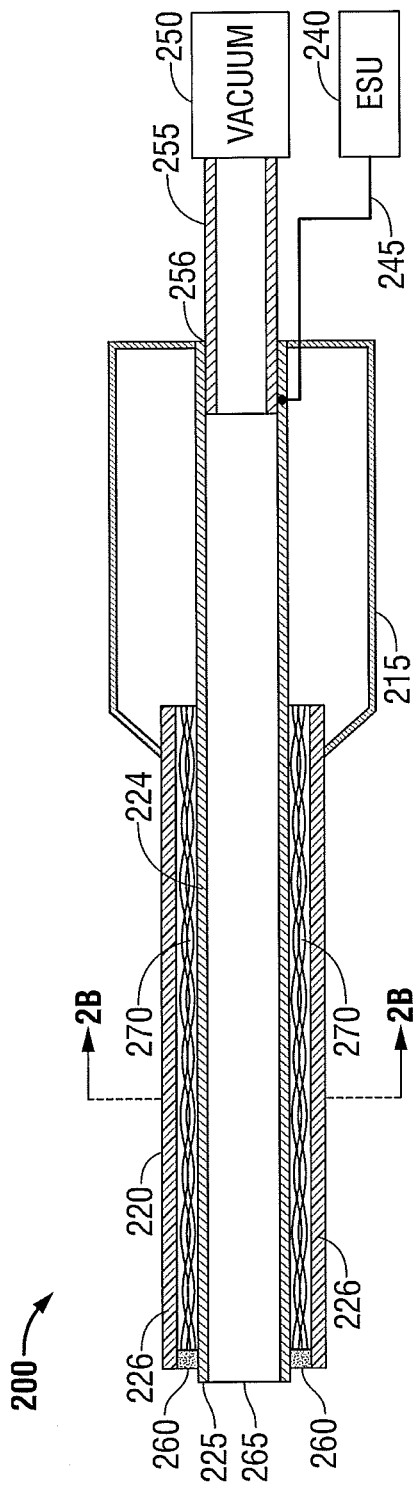
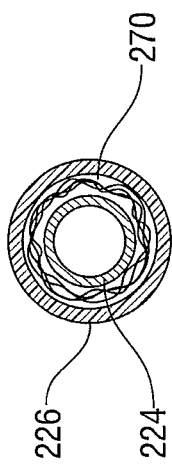
FIG. 2A
FIG. 2B

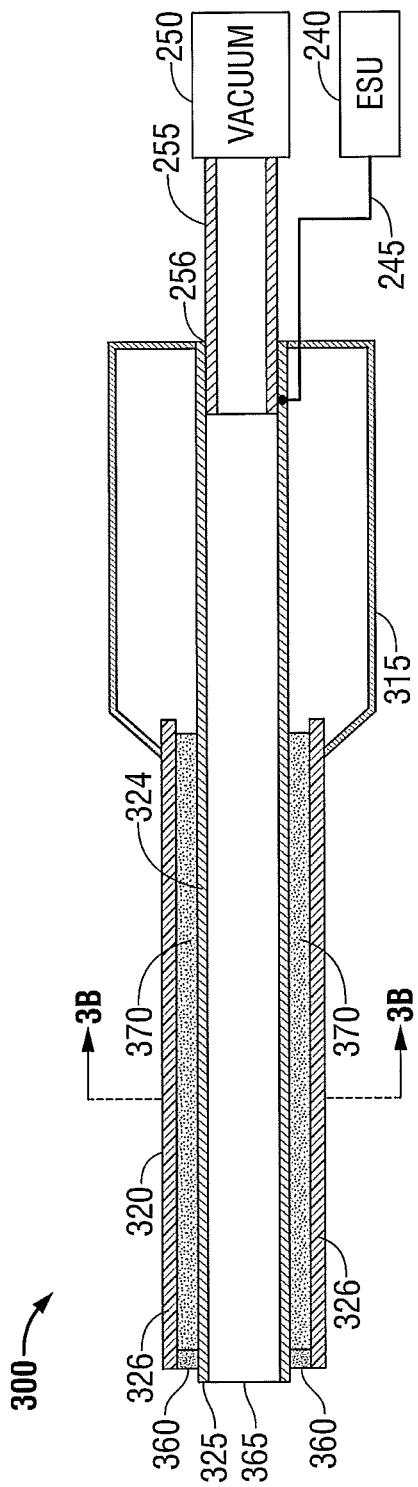
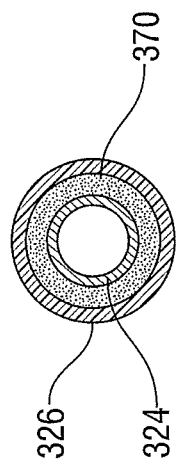
FIG. 3A
FIG. 3B

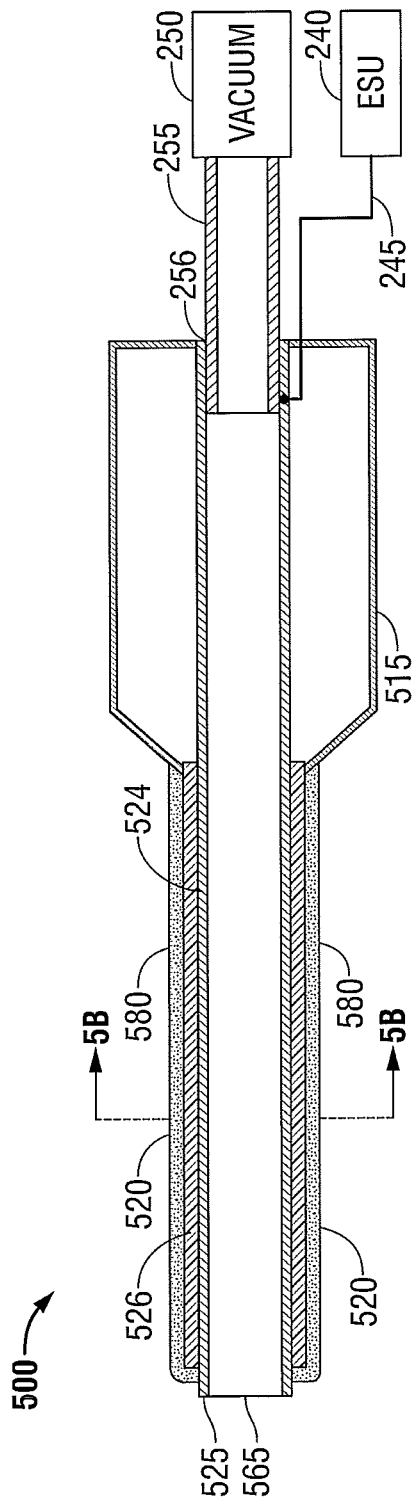
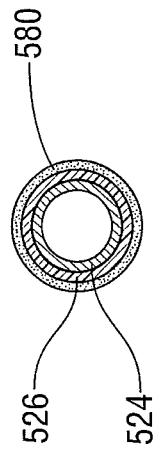
FIG. 5A
FIG. 5B

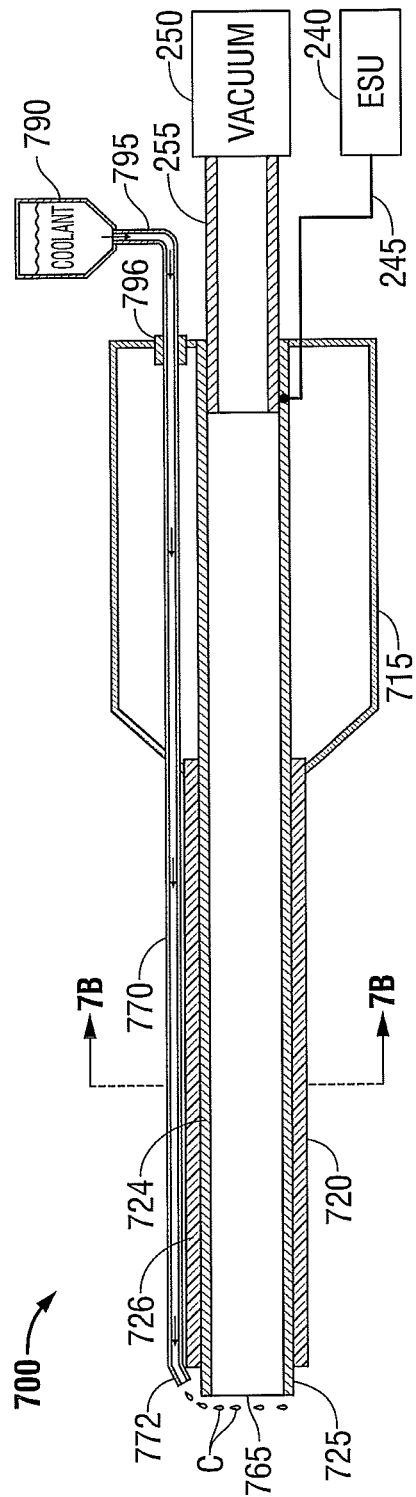
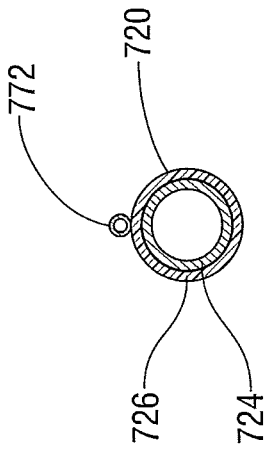
FIG. 7A
FIG. 7B

SUCTION COAGULATOR

CROSS-REFERENCE TO RELATED APPLICATION

This application is a divisional of U.S. patent application Ser. No. 12/179,206, entitled "SUCTION COAGULATOR", filed Jul. 24, 2008, now U.S. Pat. No. 8,328,804, by David N. Heard et al., the entirety of which is hereby incorporated by reference herein for all purposes.

BACKGROUND

1. Technical Field

The present invention relates generally to electrosurgical coagulators and, more particularly, to an electrosurgical suction coagulator having improved thermal insulation between the active electrode and adjacent tissue.

2. Background of Related Art

The coagulation of bleeding blood vessels and tissue using electrically conductive suction tubes is a technique which has been widely used for some time. Typically, a combination electrosurgery and suction device is employed in surgery wherever excessive blood must be removed from the bleeding site in order to facilitate hemostasis of any bleeding vessels. More particularly, during any given surgical procedure, several layers of tissue usually must be penetrated to reach the operative field. When resecting an organ, for example, a gallbladder, the tissue surrounding the organ must be penetrated and dissected before the organ can be removed. The tissues being dissected, however, often contain blood vessels, nerves, lymph vessels, and the like, which should not be severed. The technique of blunt dissection is often used to prevent unnecessary damage caused by severing these vessels or nerves.

Blunt dissection, as opposed to sharp dissection, involves the use of a blunt surface to break through the tissue, thereby preventing the damage and bleeding caused by lasers and scalpels, the tools of sharp dissection. Hard surgical sponges, generally known as peanuts or Kittner sponges, or a surgeon's fingers are often used as blunt dissectors. A peanut is a tightly wound ball of absorbent material, such as gauze or other woven cotton, which is typically gripped with forceps and acts to abrade the tissue being dissected so that the dissection can be performed by either pulling on the tissue or by forcing the peanut through the tissue.

Laparoscopy, surgery performed through several small incisions made in the body rather than through a single large opening, has become the preferred method of performing certain procedures due to the reduced trauma and risk of infection as compared to normal, open surgical procedures. As a result, the use of conventional blunt dissectors, such as the peanut, during laparoscopic procedures presents many significant drawbacks. For instance, peanuts, being secured only by forceps, can become loose in the body. Further, the view of the operative field often becomes obstructed by pieces of tissue, blood and other bodily fluids produced during blunt dissection, necessitating the immediate need for both irrigation and aspiration of the operative field. Since it is undesirable to create additional incisions, the dissection must be stopped, the dissector must be removed, and an irrigator and/or aspirator must be inserted to remove the fluid and debris.

The use of electrical energy including radiofrequency and microwave energy and, in particular, radiofrequency ("RF") electrodes or microwave antennae for ablation of tissue in the body or for the treatment of pain is known. For example, electrosurgery is a technique of using alternating current electrical signals in the approximately 200 kHz-3.3 mHz range that are generated by a source of electrosurgical energy, such as an electrosurgical generator, in connection with surgical instruments, to cut or coagulate biologic tissue endogenically. This electrosurgical signal can be a sinusoidal waveform operating in a continuous mode at a 100% duty cycle, or pulse modulated at a duty cycle of less than 100%. Typically, electrosurgical signals are operated at 100% duty cycle for maximal cutting effect, and are pulse modulated at duty cycles ranging from 50% to 25% for less aggressive cutting, or, at a substantially lower duty cycle of approximately 6%, for coagulating. The electrosurgical carrier signal may also be varied in intensity. The electrosurgical signal is applied to the patient via electrodes in either monopolar mode, or bipolar mode. In monopolar mode, the active electrode is the surgical instrument at the surgical site, and the return electrode is elsewhere on the patient, such that the electrosurgical signal passes through the patient's body from the surgical site to the return electrode. In bipolar mode, both the active and return electrodes are at the surgical site, such as with an instrument having an array of electrodes, so that the electrosurgical signal passes only through the tissue situated between the RF electrodes of the instrument.

Electrosurgical suction coagulators which both coagulate and dissect tissue have also been available for some time. Generally, these devices include a shaft formed from a conductive suction tube electrode having an electrically insulating coating over all but a most distal portion of the tube, so that the distal portion forms a generally annular ablating electrode. The shaft may be formed of malleable materials to enable a surgeon to bend the shaft to a desired shape. The distal end can be used as a blunt dissection device and/or a blunt coagulator. A suction source is attached to a proximal portion of the tube for evacuating excess fluid and debris from the surgical site through the distal end of the tube. The electrode is operably coupled to a source of electrosurgical energy, such as an electrosurgical generator.

The described electrosurgical suction coagulators may have drawbacks. In particular, heat conducted from the suction tube electrode to the outer surface of the shaft may cause the surface of the shaft to reach temperatures of 60° C. or greater. This may be a concern during surgical procedures, such as an electrosurgical adenotonsillectomy, where the shaft of a suction coagulator may be in proximity to, or in contact with, anatomical structures unrelated to the procedure, such as the uvula or the oral commissure. The elevated shaft temperature may have undesirable effects on such unrelated anatomical structures, including uvular edema and erythema of the oral commissure area. An electrosurgical suction coagulator which avoids or minimizes such undesirable effects would be a welcome advance in the art, particularly when such benefits are realized in a rugged, reliable, and relatively simple design.

SUMMARY

The present disclosure provides an electrosurgical suction coagulation system having, and related methods for, improved control of the shaft surface temperature. In particular, embodiments in accordance with the present disclosure may provide passive thermal insulation of the shaft, active cooling of the shaft, and may advantageously include combinations of passive insulation and active cooling, as will be described hereinbelow.

In an embodiment in accordance with the present disclosure, an electrosurgical suction coagulator includes a shaft formed from a conductive suction tube, an outer dielectric sheath covering over all but a distal electrode portion of the tube, and has disposed therebetween an insulating layer formed from braided material having low thermal conduction, for example, braided polymeric or ceramic fibers. The braided material may be configured as a tubular braided sheath or a spiral wrapped layer. The combination of air voids in the braided layer and the low thermal conductive properties of the braided insulating material may reduce thermal conduction from the metallic suction tube to the exterior surface of the instrument. In envisioned embodiments, an insulating layer may be formed from woven material.

In embodiments, the shaft of a suction coagulator in accordance with the present disclosure may be straight or contoured. The shaft may additionally be formed from malleable materials to enable a user, for example, a surgeon or clinician, to bend the shaft to a desired shape. A suction coagulator in accordance with the present disclosure may include a handle. The handle may include at least one control for activating the electrosurgical energy and/or evacuation (i.e., suction).

In envisioned embodiments, a suction coagulator includes thermal isolation between a suction tube and a distal electrode tip, formed from, for example without limitation, ceramic insulating material and/or polymeric insulating material. The tip may be operably coupled to the suction tube by at least one electrically conductive element, such as a wire. Additionally or alternatively, a distal electrode tip may be operably coupled to a source of electrosurgical energy by at least one of a wire and the suction tube.

In another envisioned embodiment, an insulating layer disposed between the tubular electrode and dielectric sheath is formed from closed-cell foam material, for example, closed cell foamed polyurethane. Additionally or alternatively, the outer surface of the dielectric sheath may include a closed cell foam covering disposed thereupon, which may further reduce thermal conduction from the electrode to adjacent tissue.

In embodiments, the outer surface of the dielectric sheath may include an open cell foam covering disposed thereupon. During use, the open foam layer may be infused with a fluid, for example, water or saline solution, which may increase the thermal mass of the covering and provide a cooling effect, thereby reducing surface temperature of the instrument shaft.

In embodiments, an electrosurgical generator in accordance with the present disclosure may be configured to limit the activation time of a suction coagulator, and/or enforce minimum quiescent times between activations. During use, the electrosurgical generator may determine whether the activation time has exceeded a threshold, and in response thereto, deactivate the generator. Additionally, reactivation of the generator may be inhibited until the expiration of a "rest" time period, or until a user input is received by the generator.

The instrument may be configured to provide instrument identification information to the generator, for example, an optical code (i.e., barcode), an RFID tag, or other suitable machine- or human-readable encodings. The generator may use such instrument identification information to determine corresponding activation and quiescent time parameters for the instrument.

In an envisioned embodiment, a suction coagulator in accordance with the present disclosure includes a sensor that is adapted to sense the surface temperature of the instrument. The sensor may be operably coupled to an electrosurgical generator. The electrosurgical generator may be configured to respond to the sensed temperature, by, for example, limiting the activation time, altering the electrosurgical signal, and/or deactivating the generation of the electrosurgical signal. In embodiments, the generator may additionally or alternatively respond to at least one parameter related to the sensed temperature of the instrument, for example, a change in temperature of the instrument and/or a rate of change of temperature of the instrument.

In embodiments, an electrosurgical generator in accordance with the present disclosure may be configured to issue a prompt (e.g., an alarm) to the user. A prompt may be issued to advise the user to pause the activation of the instrument. In envisioned embodiments, a prompt may be issued to advise the user to replenish depleted fluids in, for example, a fluid-infused open foam cover. Such a prompt may be based upon, for example, cumulative activation time, instrument identity, and/or the surface temperature of the instrument. The alarm may be automatically cleared after a predetermined time period. Additionally or alternatively, the alarm may be cleared by a user input received by the electrosurgical generator.

Other embodiments according to the present disclosure are envisioned wherein an electrosurgical suction coagulator includes a conduit for introducing a coolant, for example, saline solution, to the distal tip of the instrument during use. The conduit may be configured to "drip" coolant onto an electrode disposed at the distal end of the instrument. The conduit may be in fluid communication, preferably at the proximal end of the instrument, to a source of cooling fluid, for example, a saline bag, that may provide cooling fluid via any suitable manner of delivery, for example, by gravity feed, pump, or pressurized vessel.

In other envisioned embodiments, en electrosurgical suction coagulator according the present disclosure includes a coolant jacket that may be formed by a conduit included in the instrument. Coolant is introduced into the coolant jacket, preferably at the proximal end of the instrument, flows through the conduit towards the distal tip region of the instrument, and exits the instrument. The coolant jacket may be configured to cool the tip and/or the surface of the instrument.

BRIEF DESCRIPTION OF THE DRAWINGS

The above and other aspects, features, and advantages of the present disclosure will become more apparent in light of the following detailed description when taken in conjunction with the accompanying drawings in which:

FIG. 2A is a side cutaway view of an exemplary embodiment of an electrosurgical suction coagulator in accordance with the present disclosure having a braided insulation region;

FIG. 2B is a section view of the electrosurgical suction coagulator of FIG. 2A;

FIG. 3A is a side cutaway view of another exemplary embodiment of an electrosurgical suction coagulator in accordance with the present disclosure having a closed cell foam insulation region;

FIG. 3B is a section view of the electrosurgical suction coagulator of FIG. 3A;

FIG. 5A is a side cutaway view of still another exemplary embodiment of an electrosurgical suction coagulator in accordance with the present disclosure having an outer closed cell foam insulation region;

FIG. 5B is a section view of the electrosurgical suction coagulator of FIG. 5A;

FIG. 7A is a side cutaway view of another exemplary embodiment of an electrosurgical suction coagulator in accordance with the present disclosure having a lumen to deliver coolant to the distal end thereof;

FIG. 7B is a section view of the electrosurgical suction coagulator of FIG. 7A;

DETAILED DESCRIPTION

Figure 1:
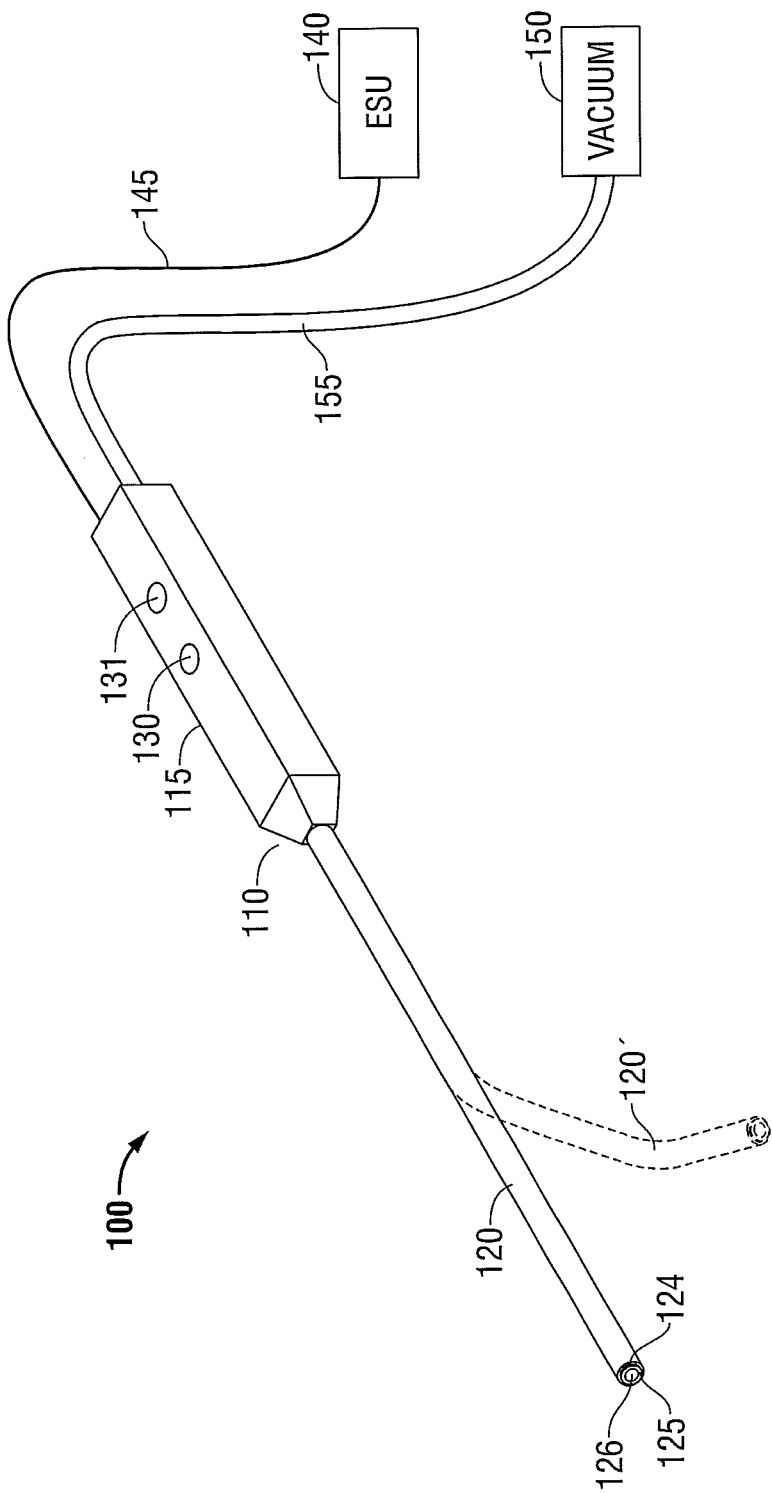
FIG. 1 is an oblique view of an exemplary embodiment of an electrosurgical suction coagulator system in accordance with the present disclosure.

Particular embodiments of the present disclosure will be described herein with reference to the accompanying drawings. As shown in the drawings and as described throughout the following description, and as is traditional when referring to relative positioning on an object, the term "proximal" refers to the end of the apparatus that is closer to the user and the term "distal" refers to the end of the apparatus that is further from the user. In the following description, well-known functions or constructions are not described in detail to avoid obscuring the present disclosure in unnecessary detail.

With reference to FIG. 1, an electrosurgical suction coagulator system 100 is presented having a suction coagulator 110 that is operably coupled to an electrosurgical generator 140 via a conductor 145. Suction coagulator 110 is operably coupled to a vacuum source 150 by a lumen 155. Suction coagulator 110 includes a handle 115 disposed at the proximal end thereof and a elongated shaft 120 extending distally from the handle 115. The shaft 120 may be formed from material having malleable or flexible properties, for example without limitation, metallic material such as aluminum and alloys thereof and/or polymeric materials such as polyurethane (PU) or polyvinyl chloride (PVC). A shaft 120 thus formed may be bent to a desired shape by the user, as shown by way of example by bent shaft 120'.

Distal end 124 of shaft 120 includes an exposed tubular electrode 125 for delivering electrosurgical energy to tissue, the electrode 125 having a conduit 126 defined longitudinally therethrough for providing suction to a surgical site. Conduit 126 is in fluid communication with vacuum source 150 via lumen 155.

In an embodiment, handle 115 may include a control 130 which may be a handswitch for controlling the application of electrosurgical energy, i.e., activation and deactivation of an electrosurgical signal. Handle 115 may include an additional or second control 131 for controlling the application of suction to the surgical site. In embodiments, control 131 may be operably coupled to a valve (not shown) that may be disposed within handle 115, shaft 120, vacuum source 150, and/or lumen 155. In other envisioned embodiments, control 131 may be operably coupled to a regulator, motor control, or other suitable manner of vacuum control.

Turning now to FIGS. 2A and 2B, a suction coagulator 200 in accordance with the present disclosure includes a housing 215 disposed proximally to an elongated shaft 220. Housing 215 may be a handle. Shaft 220 includes an insulating sheath 226 formed from any suitable dielectric material, for example, polymeric materials such as PU, PVC and the like. Shaft 220 includes a conductive tube 224 disposed coaxially within insulating sheath 226 and having a tubular distal tip electrode 225 protruding distally from insulating sheath 226 to form at least one aspiration port 265. Conductive tube 224 may be formed from any suitable electrically conductive material, including without limitation, aluminum or stainless steel. An insulator 270 having a generally cylindrical shape is disposed between conductive tube 224 and insulating sheath 226. Insulator 270 may be formed from any suitable heat-insulating material, for example without limitation, high-temperature polymers, ceramic fiber, or mineral fiber. Insulator 270 may be constructed from braided, woven, spun-woven, or randomly dispersed materials. An isolator 260 is disposed between distal tip electrode 225 and conductive tube 224 to thermally insulate the distal tip electrode 225 from the conductive tube 224 and to position distal tip electrode 225 coaxially with the distal end of insulating sheath 226. Distal tip electrode 225 and conductive tube 224 are operably connected by a conductive element 227, which may be a wire or a strap, to facilitate the delivery of electrosurgical energy to a surgical site (not shown) by distal tip electrode 225. In an embodiment, isolator 260 may be formed of heat-resistant material, for example, ceramic material. In other envisioned embodiments, isolator 260 is integrally formed with sheath 226. In use, insulator 270 acts to insulate the outer surface of sheath 226 from thermal energy that may propagate from, for example, the surgical site (not explicitly shown), distal tip electrode 225, and/or conductive tube 224. Vacuum source 250 may be selectively activated to provide aspiration suction to tube 224 and tip 225 to facilitate the removal of biodebris from the surgical site (not explicitly shown).

In another envisioned embodiment best illustrated in FIGS. 3A and 3B, a suction coagulator 300 includes an elongated shaft 320 supported by a housing 315, the shaft 320 further including an insulator 370 having a generally cylindrical shape that is longitudinally disposed between a conductive tube 324 and a dielectric sheath 326. Insulator 370 may be formed from a closed cell foam material, for example without limitation, closed cell polyurethane foam. A tubular distal tip electrode 325 extends from the distal end of shaft 320 to form at least one aspiration port 365. An isolator 360 is disposed between distal tip electrode 325 and conductive tube 324 to thermally insulate the distal tip electrode 325 from the conductive tube 324 and additionally to position distal tip electrode 325 coaxially with the distal end of dielectric sheath 326. Distal tip electrode 325 and conductive tube 324 are operably coupled by a conductive element 327, which may be a wire or a strap. In an embodiment, isolator 360 may be formed of heat-resistant material, for example, ceramic. In other envisioned embodiments, seal 360 may be integrally formed with sheath 326.

Figure 4A:
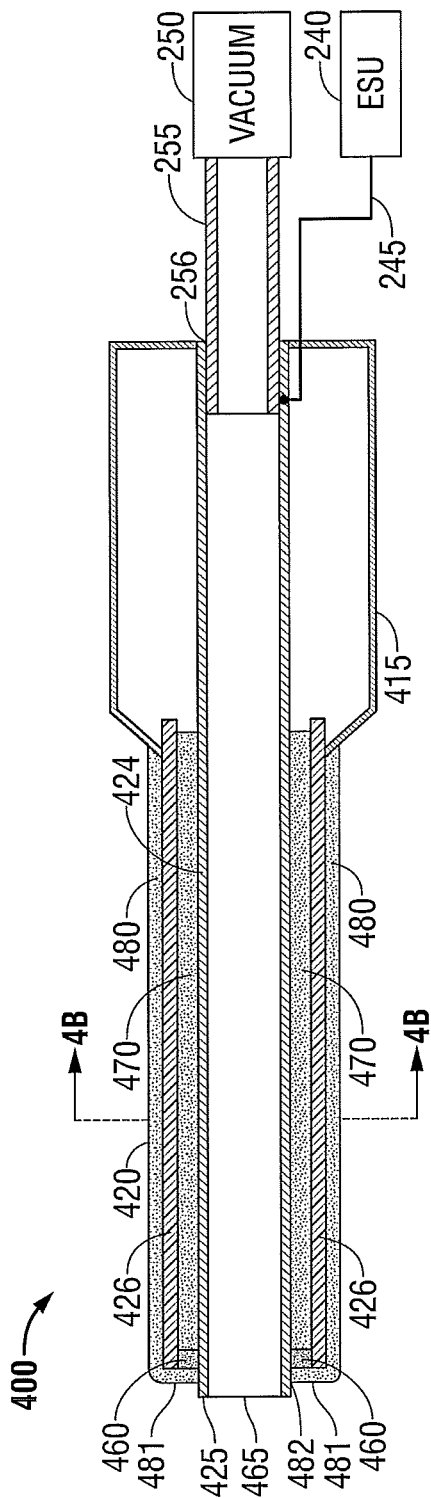
FIG. 4A is a side cutaway view of yet another exemplary embodiment of an electrosurgical suction coagulator in accordance with the present disclosure having an inner closed cell foam insulation region and an outer closed cell foam insulation region.
Figure 4B:
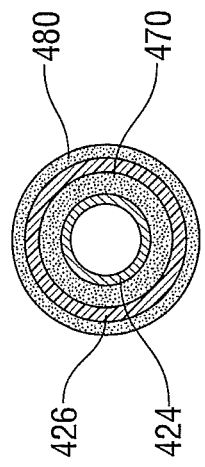
FIG. 4B is a section view of the electrosurgical suction coagulator of FIG. 4A.

In yet another envisioned embodiment best illustrated in FIGS. 4A and 4B, a suction coagulator 400 includes an elongated shaft 420 that is supported by a housing 415. The shaft 420 includes an insulator 470 having a generally cylindrical shape that is longitudinally disposed between a conductive tube 424 and a dielectric sheath 426, and an insulator 480 having a generally cylindrical shape that is longitudinally disposed around dielectric sheath 426. A tubular distal tip electrode 425 extends from the distal end of shaft 420 to form at least one aspiration port 465. Insulators 470, 480 may be formed from a closed cell foam material, for example without limitation, closed cell polyurethane foam. In use, insulators 470, 480 act to insulate the outer surface of shaft 420 from thermal energy that may propagate from, for example, the surgical site, distal tip electrode 425, and/or conductive tube 424. An isolator 460 is disposed between distal tip electrode 425 and conductive tube 424 to thermally insulate the distal tip electrode 425 from the conductive tube 424 and additionally to position distal tip electrode 425 coaxially with the distal end of dielectric sheath 426. Distal tip electrode 425 and electrode 424 are operably coupled by a conductive element 427, which may be a wire or a strap. Insulator 480 may include at the distal end thereof an annular insulating region 481 that encloses the distal end 425 of dielectric sheath 426 and/or isolator 460. In embodiments, annular insulating region 481 may be joined to electrode 425 by a bonded region 482, for example, by adhesive, heat weld, or crimp.

Turning to FIGS. 5A and 5B, yet another embodiment according to the present disclosure is illustrated wherein a suction coagulator 500 includes an elongated shaft 520 that is supported by a housing 515. The shaft 520 further including a tubular electrode 524 having generally cylindrical sheath 526 longitudinally disposed around the outer surface thereof. An insulator 580 is concentrically disposed around sheath 526. Insulator 580 may be formed from a closed cell foam material, for example without limitation, closed cell polyurethane foam. In use, insulator 580 acts to reduce the propagation of thermal energy from, for example, the surgical site, an electrode tip 525, and/or electrode 524, to the outer surface of shaft 520.

Figure 6A:
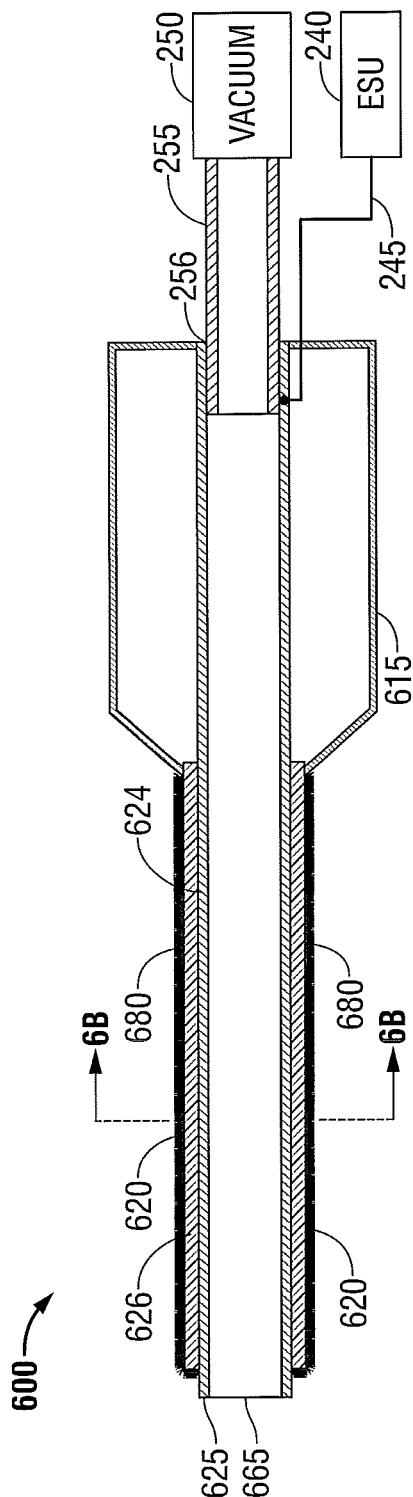
FIG. 6A is a side cutaway view of another exemplary embodiment of an electrosurgical suction coagulator in accordance with the present disclosure having an outer open cell foam insulation region.
Figure 6B:
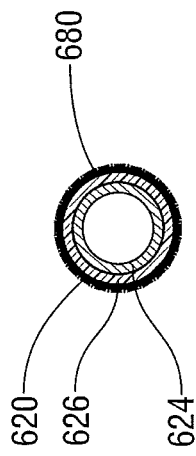
FIG. 6B is a section view of the electrosurgical suction coagulator of FIG. 6A.

In FIGS. 6A and 6B there is illustrated an envisioned embodiment of a suction coagulator 600 in accordance with the present disclosure wherein an elongated longitudinal shaft 620 is supported by a housing 615. An open cell foam cover 680 surrounds shaft 620. The shaft 620 includes a tubular electrosurgical electrode 624 disposed longitudinally therethrough, the tubular electrosurgical electrode 624 having an exposed tip 625 for delivering electrosurgical energy to tissue. A generally cylindrical sheath 626 is longitudinally disposed around substantially all but the exposed tip 625 of tubular electrosurgical electrode 624. Electrode 624 is in fluid communication with the source of vacuum 250 for the aspiration of biodebris, for example, tissue, eschar, blood and/or other bodily fluids. During use, the open cell foam cover may be infused with a fluid (not explicitly shown) for example, water or saline solution. The fluid may increase the thermal mass of the covering and, additionally or alternatively, may provide a cooling effect. In this manner, an increase in surface temperature of the instrument shaft may be diminished or precluded, thereby reducing the risk of undesirable effects on adjacent anatomical structures.

In FIGS. 7A and 7B, there is shown an envisioned embodiment wherein a suction coagulator 700 includes an elongated shaft 720 that is supported by a housing 715. The shaft 720 includes a tubular electrosurgical electrode 724 disposed longitudinally therethrough, the tubular electrosurgical electrode 724 having an exposed tip 725 for delivering electrosurgical energy to tissue. A generally cylindrical sheath 726 is longitudinally disposed around substantially all but the exposed tip 725 of tubular electrosurgical electrode 724. At least one cooling lumen 770 is disposed longitudinally on the shaft 720 for delivering coolant C to the distal region, i.e., electrode 725 of suction coagulator 700. Cooling lumen 770 is in fluid communication with a reservoir 790 via a conduit 795. In embodiments, a connector 796 is provided for coupling a conduit 795 to cooling lumen 770. Reservoir 790 may contain a coolant, for example without limitation, saline or water. In use, coolant C may flow from reservoir 790 through conduit 795, lumen 770, and discharge from distal end 772 of lumen 770. A valve (not explicitly shown) may be provided to regulate the flow of coolant. The valve (not explicitly shown) may be caused to be actuated by a user and/or by an automated controller, such as a processor. Coolant C may flow from reservoir 790 via gravity feed (i.e., "drip" feed) and/or by pressure feed provided by, for example without limitation, a centrifugal pump, a positive displacement pump, or a peristaltic pump (not explicitly shown).

Figure 8A:
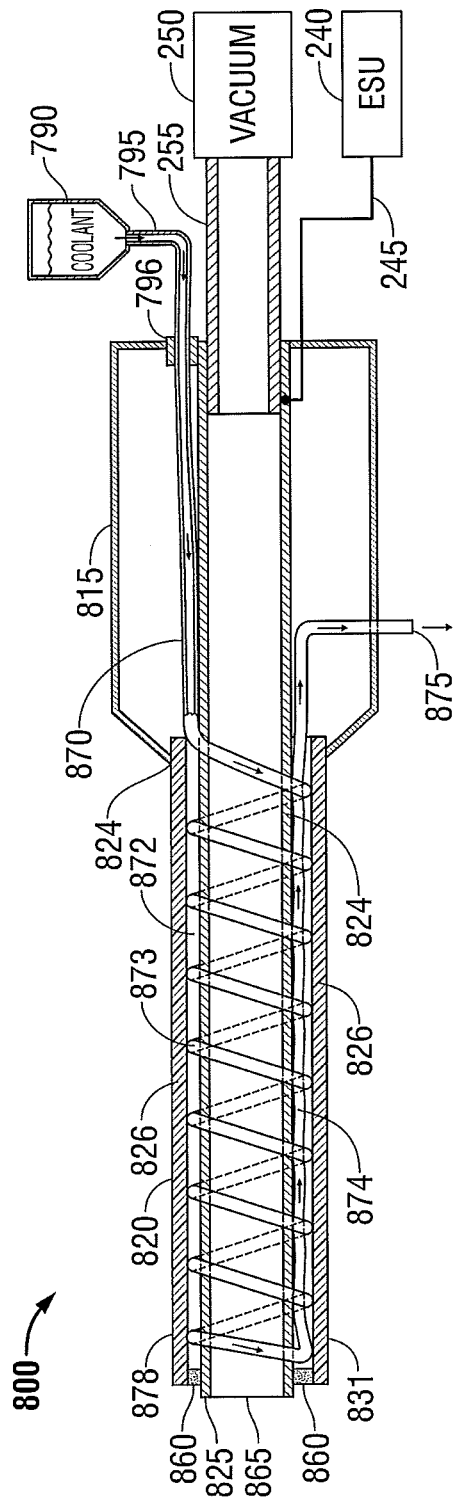
FIG. 8A is a side cutaway view of an exemplary embodiment of an electrosurgical suction coagulator in accordance with the present disclosure having a spiral coolant jacket.
Figure 8B:
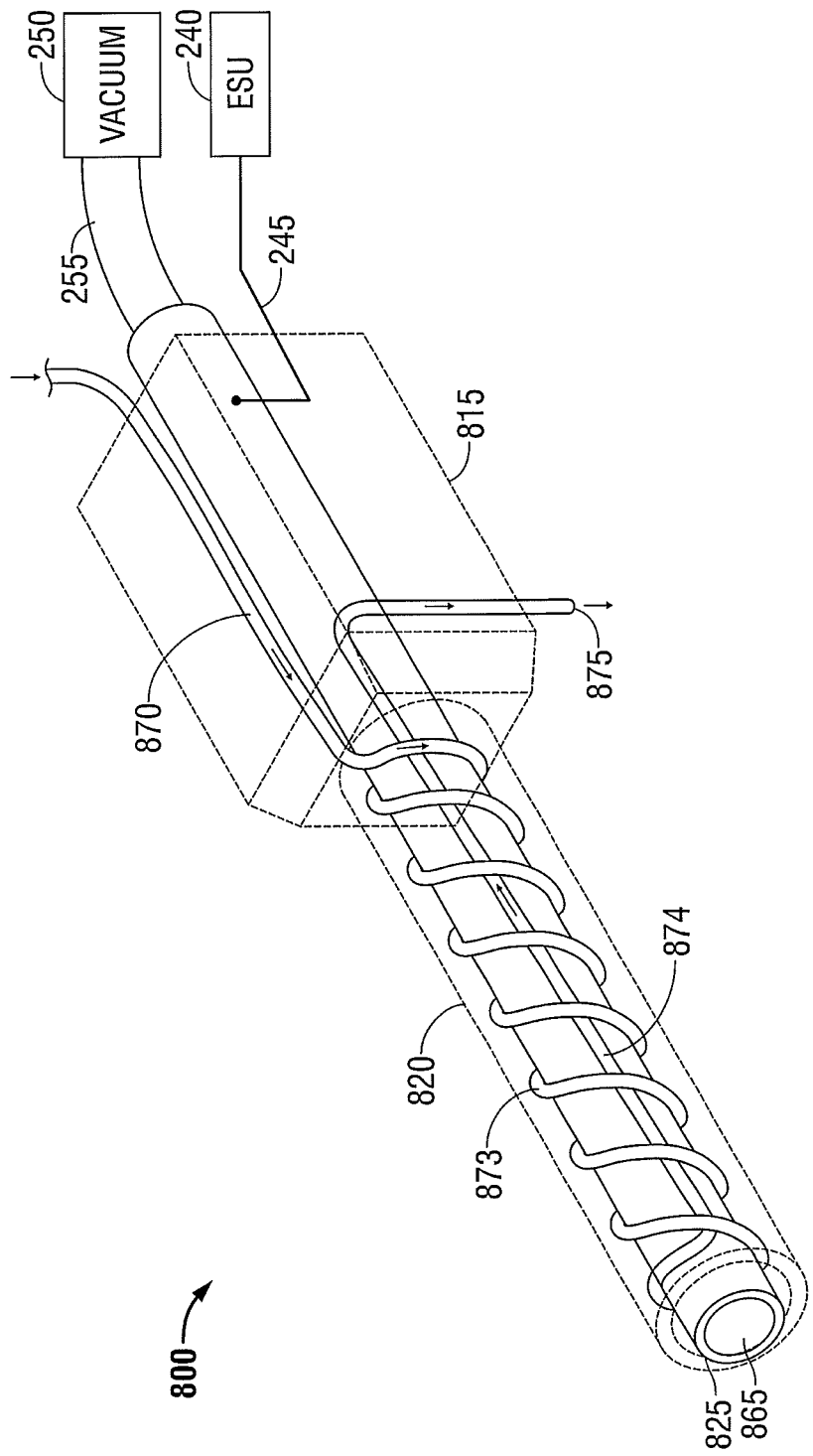
FIG. 8B is an oblique view of the exemplary electrosurgical suction coagulator of FIG. 8A.

Turning now to FIGS. 8A and 8B, another envisioned embodiment of a suction coagulator 800 in accordance with the present disclosure is illustrated wherein a proximal housing 815 supports an elongated shaft 820 extending distally therefrom. A generally tubular cover 826 is longitudinally disposed around substantially all but an exposed tip 825 of a tubular electrosurgical electrode 824 that is disposed longitudinally through shaft 820. A region 871 between cover 826 and electrode 824 defines a cooling jacket 872 that surrounds the tubular electrode 824. As best shown in FIGS. 8A and 8B, a cooling jacket 872 may include a cooling lumen 873 having a generally helical shape, and having an inlet port 870 and an outlet port 875. The helical coils formed by cooling lumen 873 may form an open helix, wherein the helix pitch is greater than the outer diameter of the cooling lumen 873, or a closed helix wherein the helix pitch is substantially equal to the outer diameter of the cooling lumen 873. Inlet port 870 is in fluid communication with a coolant source 790 via a conduit 795. Coolant C may be any biocompatible fluid, for example without limitation, saline, water, or air. Coolant C may flow from coolant source 790 via gravity feed (i.e., "drip" feed) and/or by pressure feed provided by, for example, a pump, as previously described herein. In one embodiment, coolant flows distally though the helical cooling lumen 873 until the distal end 878 of jacket 872 is reached. Coolant C then flows proximally through a return lumen 874 to outlet port 875, whereupon the coolant exits the suction coagulator 800. In another embodiment, coolant C flow may be reversed from that described hereinabove, i.e., coolant may flow initially to distal end 878 and thereafter proceed proximally through helical cooling lumen 873, and subsequently, discharged from the suction coagulator 800 at outlet port 875. In this manner, a cooling effect can be selectively biased towards a proximal end of the shaft or a distal end of the shaft as desired. For example, in use during an electrosurgical procedure such as an adenotonsillectomy, coolant C may be caused flow distally wherein fresh coolant is introduced to cooling jacket 872 at the proximal end thereof. Thus a cooling effect may be biased toward a proximal end 830 of shaft 820, which may be adjacent to, for example, anatomical structures unrelated to the electrosurgical procedure, such as the uvula and the oral commissure area, thereby reducing the risk of undesired effects to such areas. Alternatively, cooling may be biased towards a distal end 831 of shaft 820 by causing coolant to flow proximally by introducing coolant C to cooling jacket 872 at the distal end thereof. In embodiments, the direction of coolant C flow may be selected by causing a reversing valve (not explicitly shown) that is in fluid communication with cooling jacket 872 to be actuated in a manner consistent with the desired direction of coolant C flow.

Figure 9A:
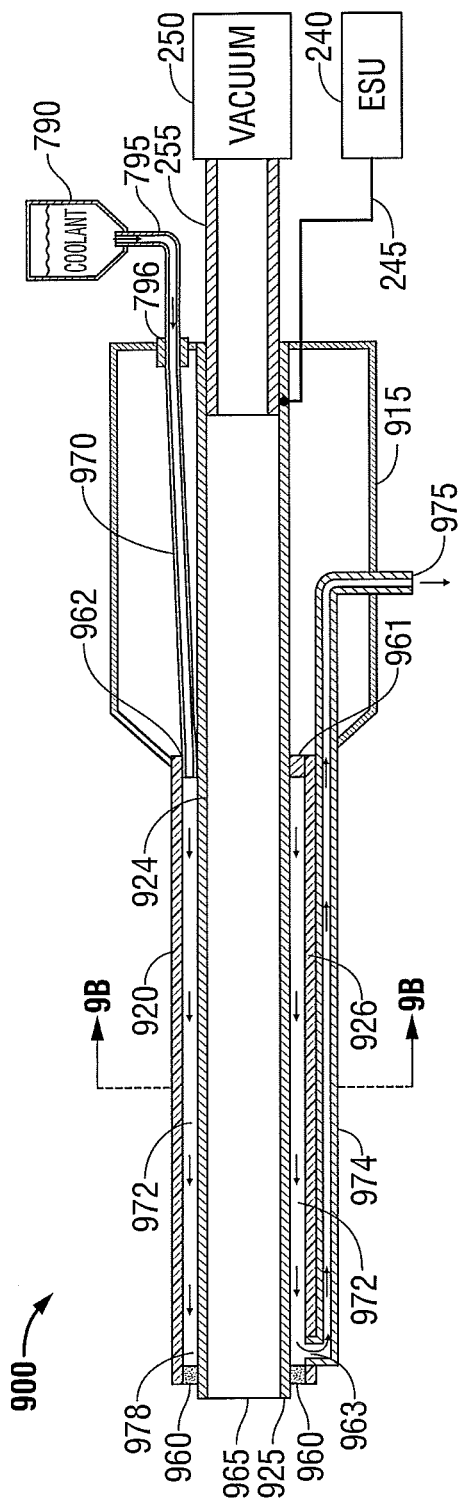
FIG. 9A is a side cutaway view of an exemplary embodiment of an electrosurgical suction coagulator in accordance with the present disclosure having a cylindrical coolant jacket.
Figure 9B:
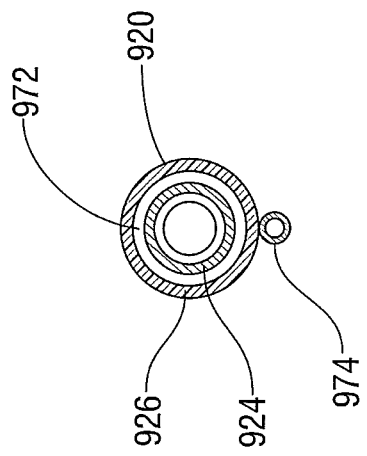
FIG. 9B is a section view of the electrosurgical suction coagulator of FIG. 9A.

FIGS. 9A and 9B illustrate still another envisioned embodiment of a suction coagulator 900 in accordance with the present disclosure is illustrated, the suction coagulator including a distal housing 915 having extending distally therefrom an elongated shaft 920. Shaft 920 includes a cooling jacket 972 that is formed by the generally cylindrical region longitudinally disposed between a tubular electrode 924 and a tubular cover 926. The cooling jacket is sealed at the distal end thereof by distal seal 960 and at the proximal end thereof by proximal seal 961. A cooling supply lumen 970 is in fluid communication with the cooling jacket via an inlet port 962 provided by proximal seal 961. During use, coolant C is admitted into cooling jacket 972 at the proximal end thereof, and thereafter flows distally. A distal return opening 963 is provided by cover 926, or additionally or alternatively, by distal seal 960. Supply end 870 is in fluid communication with a coolant source 790 via a conduit 795. Coolant C may be any biocompatible fluid, for example without limitation, saline, water, or air. Coolant C may flow to cooling jacket 972 via conduits 970, 995 from coolant source 990 via gravity feed (i.e., "drip" feed) and/or by pressure feed provided by, for example, a pump, as previously described herein. In one embodiment, coolant C flows distally though the cooling jacket 972 until the distal end 978 of jacket 972 is reached. Coolant C then flows through distal return opening 963, proximally through a return lumen 974 to outlet port 975, whereupon the coolant exits the suction coagulator 900. In another embodiment, coolant C flow may be reversed from that described hereinabove, i.e., coolant C may flow initially to distal end 978 and thereafter proceed proximally through cooling jacket 972, and subsequently, discharged from the suction coagulator 900 at outlet port 975. The direction of coolant flow may be selectively reversed as previously described herein.

The described embodiments of the present disclosure are intended to be illustrative rather than restrictive, and are not intended to represent every embodiment of the present disclosure. Further variations of the above-disclosed embodiments and other features and functions, or alternatives thereof, may be made or desirably combined into many other different systems or applications without departing from the spirit or scope of the disclosure as set forth in the following claims both literally and in equivalents recognized in law.

What is claimed is:

1. An electrosurgical suction coagulator, comprising:
   a housing having proximal and distal ends and a substantially malleable elongated tube like shaft extending longitudinally from the distal end thereof, the substantially malleable elongated tube-like shaft including:
   a tube-like dielectric sheath;
   a tube-like conductor disposed coaxially through the tube-like dielectric sheath and configured to operably couple to a source of electrosurgical energy, the tube-like conductor having at a distal end thereof at least one tube aspiration port defined therein, the tube-like conductor being adapted at a proximal end thereof to operably couple to a source of aspiration suction;
   an electrode tip disposed distal to the tube-like conductor and separated from the tube-like conductor by an isolator configured to thermally insulate the electrode tip from the tube-like conductor, the electrode tip in electrical communication with the tube-like conductor through the isolator, wherein the electrode tip and isolator further define a tip aspiration port that is in fluid communication with the tube aspiration port; and
   a cooling jacket disposed about the tube-like conductor, the cooling jacket having an inlet port and an outlet port, wherein the inlet port is configured to operably couple to a source of coolant and the outlet port is configured to expel coolant from the electrosurgical suction coagulator.

2. An electrosurgical suction coagulator according to claim 1 wherein the cooling jacket includes a lumen having a substantially helical shape disposed concentrically around the tube-like conductor.

3. An electrosurgical suction coagulator according to claim 1 wherein the cooling jacket includes a chamber having a substantially cylindrical shape disposed concentrically around the tube-like conductor.

* * * * *